(12) United States Patent
Bower et al.

(10) Patent No.: US 8,927,250 B2
(45) Date of Patent: *Jan. 6, 2015

(54) POLYPEPTIDES HAVING ALPHA-AMYLASE AND GRANULAR STARCH HYDROLYZING ACTIVITY

(75) Inventors: Benjamin S. Bower, Palo Alto, CA (US); Nigel Dunn-Coleman, El Sauzal Tenerife (ES); Suzanne E. Lantz, Palo Alto, CA (US); Cherry Lin, San Jose, CA (US); Michael Ward, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 414 days.

This patent is subject to a terminal disclaimer.

(21) Appl. No.: 13/225,266

(22) Filed: Sep. 2, 2011
(Under 37 CFR 1.47)

(65) Prior Publication Data

US 2012/0052551 A1    Mar. 1, 2012

Related U.S. Application Data

(63) Continuation of application No. 11/795,271, filed as application No. PCT/US2006/005622 on Feb. 17, 2006, now Pat. No. 8,034,600.

(60) Provisional application No. 60/654,105, filed on Feb. 18, 2005.

(51) Int. Cl.
*C12N 9/30* (2006.01)
*C12N 1/15* (2006.01)
*C07H 21/04* (2006.01)

(52) U.S. Cl.
USPC ............. 435/203; 435/254.11; 536/23.2

(58) Field of Classification Search
USPC ............... 435/203, 254.11; 536/23.2
See application file for complete search history.

(56) References Cited

U.S. PATENT DOCUMENTS

| | | | |
|---|---|---|---|
| 4,760,025 A | 7/1988 | Estell et al. | |
| 5,246,853 A | 9/1993 | Clarkson et al. | |
| 5,264,366 A | 11/1993 | Ferrari et al. | |
| RE34,606 E | 5/1994 | Estell et al. | |
| 5,475,101 A | 12/1995 | Ward et al. | |
| 5,847,276 A | 12/1998 | Mimken et al. | |
| 6,022,725 A | 2/2000 | Fowler et al. | |
| 6,268,328 B1 | 7/2001 | Mitchinson et al. | |
| 8,034,600 B2 * | 10/2011 | Bower et al. | 435/203 |
| 8,048,657 B2 * | 11/2011 | Breneman et al. | 435/162 |
| 2002/0182734 A1 | 12/2002 | Diaz-Torres et al. | |
| 2005/0054071 A1 * | 3/2005 | Udagawa et al. | 435/200 |
| 2009/0181125 A1 * | 7/2009 | Zhou et al. | 426/44 |

FOREIGN PATENT DOCUMENTS

| | | |
|---|---|---|
| EP | 215594 | 3/1987 |
| EP | 244234 | 11/1987 |
| WO | 92/06209 | 4/1992 |
| WO | 02/14490 | 2/2002 |
| WO | 2004/113551 | 12/2004 |
| WO | 2005/001036 | 1/2005 |
| WO | WO 2005/003311 * | 1/2005 |
| WO | 2005/118795 | 12/2005 |

OTHER PUBLICATIONS

Bennett and Lasure, More Gene Manipulations in Fungi, Academic Press, San Diego (1991) pp. 70-76.
Finkelstein, chapter 6 in Biotechnology of Filamentous Fungi, Finkelstein et al. Eds. Butterworth-Heinemann, Boston, MA (1992), Chap. 6.
Hopwood et al., 1985, Genetic Manipulation of Streptomyces: Laboratory Manual, The John Innes Foundation, Norwich, UK.
Kaneko, et al., Molecular Cloning and Determination of the Nucleotide Sequence of a Gene Encoding an Acid-Stable α-Amylase from *Aspergillus kawachii*, Journal of Fermentation and Bioengineering vol. 81, No. 4, (292-298) 1996.
Nevalainen et al., "The Molecular Biology of *Trichoderma* and its Application to the Expression of Both Homologous and Heterologous Genes", in Molecular Industrial Mycology, Eds. Leong and Berka, Marcel Dekker Inc., NY (1992) pp. 129-148.
Pourquie, J. et al., Biochemistry and Genetics of Cellulose Degradation, eds. Aubert, J. P. et al., Academic Press, pp. 71-86, 1988.
Sambrook et al., Molecular Cloning: A Laboratory Manual (2nd Ed., 1989), Chapters 9 and 11.
Singleton, et al., Dictionary of Microbiology and Molecular Biology, 2d Ed., John Wiley and Sons, New York (1994).
Van Den Hondel et al. (1991) in Bennett and Lasure (Eds.) More Gene Manipulations in Fungi, Academic Press pp. 396-428.

* cited by examiner

*Primary Examiner* — Kevin K. Hill
(74) *Attorney, Agent, or Firm* — Danisco US Inc.

(57) ABSTRACT

The present invention relates to a polypeptide having alpha-amylase activity obtained from a strain of *Aspergillus niger*.

12 Claims, 8 Drawing Sheets

FIGURE 1A
Aspergillus niger alpha-amylase DNA sequence
(SEQ ID NO: 1)

ATGAGACTATCGACTTCAAGTCTCTTACTTTCCGTGTCTCTGCTGGGGAAGCTGGCC
CTCGGGCTGTCGGCTGCAGAATGGCGCACTCAGTCGATTTACTTCCTATTGACGGAT
CGGTTCGGTAGGACGGACAATTCGACGACAGCTACATGCAATACGGGTGACCAAGTA
CGTTGGTATTGCAGGACTTTTATCATTCATCTACTGACTTGAATAGATCTATTGTGG
TGGTAGTTGGCAAGGGATCATCAACCATGTTTGTAACCGCTCCATACTATCTGCTGT
GCGCGTGTCTGACTTTATTTGCTGCAGCTGGATTATATCCAGGGCATGGGATTCACG
GCCATCTGGATCTCGCCTATCACTGAACAGCTGCCCCAGGATACTGCTGATGGTGAA
GCCTACCATGGATATTGGCAGCAGAAGATGTATGCGTTCCTCCTTTCCATATCGTAG
GCTTACTCTCAGACGGCGACTGACTTGACAGATACGACGTGAACTCCAACTTCGGCA
CTGCAGATGACCTCAAGTCCCTCTCAGATGCGCTTCATGCCCGCGGAATGTACCTCA
TGGTGGACGTCGTCCCTAACCACATGGTAAGTGCTGCTTCAGCATCCTAATCAGTGA
ATTCCAAGTGCCAACGCTAACTGTACCAGGGCTACGCCGGCAACGGCAACGATGTAG
ACTACAGCGTCTTCGACCCCTTCGATTCCTCCTCCTACTTCCACCCATACTGCCTGA
TCACAGATTGGGACAACTTGACCATGGTCCAAGATTGTTGGGAGGGTGACACCATCG
TATCTCTGCCAGACCTAAACACCACCGAAACTGCCGTGAGAACAATCTGGTATGACT
GGGTAGCCGACCTGGTATCCAATTATTCAGGTGCGAATTGCAATCCAATCTAAAATA
ATCATATACTAAGTGAAATCATCAGTCGACGGACTCCGCATCGACAGTGTCCTCGAA
GTCGAACCAGACTTCTTCCCGGGCTACCAGGAAGCAGCGGGTGTCTACTGCGTCGGC
GAAGTCGACAACGGCAACCCTGCCCTCGACTGCCCATACCAGGAGTACCTGGACGGC
GTCCTCAACTATCCGATGTACATTCCCCTACACATTATTCAGATCTTCGCTAACTCC
AAACCAGCTACTGGCAACTCCTCTACGCCTTCGAATCCTCCAGCGGCAGCATCAGCG
ACCTCTACAACATGATCAAATCCGTCGCAAGCGACTGCTCCGATCCGACACTACTCG
GCAACTTCATCGAAAACCACGACAATCCCCGTTTTGCCTCGTATGTCCCACCCCCTC
CCATCCCCTCCCCACAATCACACTCACTAATGCATCAAACAGCTACACATCCGACTA
CTCGCAAGCCAAAAACGTCCTCAGCTACATCTTCCTCTCCGACGGCATCCCCATCGT
CTACGCCGGCGAAGAACAGCACTACTCCGGCGGCAAGGTGCCCTACAACCGCGAAGC
GACCTGGCTCTCAGGCTACGACACCTCCGCAGAGCTCTACACCTGGATAGCCACCAC
GAACGCGATCCGCAAACTAGCCATCTCAGCTGACTCGGCCTACATTACCTACGCGGT

FIGURE 1B

TCGTCCTTCCCTCCCCCCCACCCTACAAACACCCCCACATACTAACAACATCCCAAT
AATGAAATAGAATGACGCATTCTACACCGACAGCAACACCATCGCAATGCGCAAAGG
CACCTCAGGGAGCCAAGTCATCACCGTCCTCTCCAACAAAGGCTCCTCAGGAAGCAG
CTACACCCTGACCCTCAGCGGAAGCGGCTATACATCCGGCACGAAGCTGATCGAAGC
GTATACATGCACGTCCGTGACCGTGGACTCGAGCGGCGATATCCCCGTGCCGATGGC
GTCGGGATTACCGAGAGTTCTTCTCCCCGCGTCCGTCGTCGATAGCTCTTCGCTCTG
TGGCGGGAGCGGAAGTAATTCCTCAACTACAACCACAACAACAGCTACCTCATCTTC
CACTGCGACATCCAAATCCGCATCAACCTCGTCTACGTCGACGGCATGCACAGCTAC
CTCTACCTCCCTCGCGGTCACGTTCGAAGAGCTCGTCACGACTACCTACGGGAGGA
AATCTACCTGAGCGGATCGATCTCCCAGCTTGGGGACTGGGATACGAGTGATGCGGT
GAAGATGTCCGCGGATGATTATACGTCGAGTAATCCGGAGTGGTCGGTTACTGTGAC
GTTGCCGGTGGGGACAACCTTTGAGTATAAGTTTATTAAGGTGGAGTCGGATGGGAC
TGTTACTTGGGAGAGTGATCCGAATCGGGAGTATACGGTGCCCGAGTGTGGGAGTGG
GGAGACGGTGGTTGACACTTGGAGGTAA

FIGURE 2A
cDNA sequence (SEQ ID NO: 2)

ATGAGACTATCGACTTCAAGTCTCTTACTTTCCGTGTCTCTGCTGGGGAAGCTGGCC

CTCGGGCTGTCGGCTGCAGAATGGCGCACTCAGTCGATTTACTTCCTATTGACGGAT

CGGTTCGGTAGGACGGACAATTCGACGACAGCTACATGCAATACGGGTGACCAAATC

TATTGTGGTGGTAGTTGGCAAGGGATCATCAACCATCTGGATTATATCCAGGGCATG

GGATTCACGGCCATCTGGATCTCGCCTATCACTGAACAGCTGCCCCAGGATACTGCT

GATGGTGAAGCCTACCATGGATATTGGCAGCAGAAGATATACGACGTGAACTCCAAC

TTCGGCACTGCAGATGACCTCAAGTCCCTCTCAGATGCGCTTCATGCCCGCGGAATG

TACCTCATGGTGGACGTCGTCCCTAACCACATGGGCTACGCCGGCAACGGCAACGAT

GTAGACTACAGCGTCTTCGACCCCTTCGATTCCTCCTCCTACTTCCACCCATACTGC

CTGATCACAGATTGGGACAACTTGACCATGGTCCAAGATTGTTGGGAGGGTGACACC

ATCGTATCTCTGCCAGACCTAAACACCACCGAAACTGCCGTGAGAACAATCTGGTAT

GACTGGGTAGCCGACCTGGTATCCAATTATTCAGTCGACGGACTCCGCATCGACAGT

GTCCTCGAAGTCGAACCAGACTTCTTCCCGGGCTACCAGGAAGCAGCGGGTGTCTAC

TGCGTCGGCGAAGTCGACAACGGCAACCCTGCCCTCGACTGCCCATACCAGGAGTAC

CTGGACGGCGTCCTCAACTATCCGATCTACTGGCAACTCCTCTACGCCTTCGAATCC

TCCAGCGGCAGCATCAGCGACCTCTACAACATGATCAAATCCGTCGCAAGCGACTGC

TCCGATCCGACACTACTCGGCAACTTCATCGAAAACCACGACAATCCCGTTTTGCC

TCCTACACATCCGACTACTCGCAAGCCAAAAACGTCCTCAGCTACATCTTCCTCTCC

GACGGCATCCCCATCGTCTACGCCGGCGAAGAACAGCACTACTCCGGCGGCAAGGTG

CCCTACAACCGCGAAGCGACCTGGCTCTCAGGCTACGACACCTCCGCAGAGCTCTAC

ACCTGGATAGCCACCACGAACGCGATCCGCAAACTAGCCATCTCAGCTGACTCGGCC

TACATTACCTACGCGAATGACGCATTCTACACCGACAGCAACACCATCGCAATGCGC

AAAGGCACCTCAGGGAGCCAAGTCATCACCGTCCTCTCCAACAAAGGCTCCTCAGGA

AGCAGCTACACCCTGACCCTCAGCGGAAGCGGCTATACATCCGGCACGAAGCTGATC

GAAGCGTATACATGCACGTCCGTGACCGTGGACTCGAGCGGCGATATCCCCGTGCCG

ATGGCGTCGGGATTACCGAGAGTTCTTCTCCCCGCGTCCGTCGTCGATAGCTCTTCG

CTCTGTGGCGGGAGCGGAAGTAATTCCTCAACTACAACCACAACAACAGCTACCTCA

TCTTCCACTGCGACATCCAAATCCGCATCAACCTCGTCTACGTCGACGGCATGCACA

GCTACCTCTACCTCCCTCGCGGTCACGTTCGAAGAGCTCGTCACGACTACCTACGGG

GAGGAAATCTACCTGAGCGGATCGATCTCCCAGCTTGGGGACTGGGATACGAGTGAT

FIGURE 2B

```
GCGGTGAAGATGTCCGCGGATGATTATACGTCGAGTAATCCGGAGTGGTCGGTTACT
GTGACGTTGCCGGTGGGGACAACCTTTGAGTATAAGTTTATTAAGGTGGAGTCGGAT
GGGACTGTTACTTGGGAGAGTGATCCGAATCGGGAGTATACGGTGCCCGAGTGTGGG
AGTGGGGAGACGGTGGTTGACACTTGGAGGTAA
```

FIGURE 3
Translated protein sequence (SEQ ID NO: 3)

MRLSTSSLLLSVSLLGKLALGLSAAEWRTQSIYFLLTDRFGRTDNSTTATCNTGDQI

YCGGSWQGIINHLDYIQGMGFTAIWISPITEQLPQDTADGEAYHGYWQQKIYDVNSN

FGTADDLKSLSDALHARGMYLMVDVVPNHMGYAGNGNDVDYSVFDPFDSSSYFHPYC

LITDWDNLTMVQDCWEGDTIVSLPDLNTTETAVRTIWYDWVADLVSNYSVDGLRIDS

VLEVEPDFFPGYQEAAGVYCVGEVDNGNPALDCPYQEYLDGVLNYPIYWQLLYAFES

SSGSISDLYNMIKSVASDCSDPTLLGNFIENHDNPRFASYTSDYSQAKNVLSYIFLS

DGIPIVYAGEEQHYSGGKVPYNREATWLSGYDTSAELYTWIATTNAIRKLAISADSA

YITYANDAFYTDSNTIAMRKGTSGSQVITVLSNKGSSGSSYTLTLSGSGYTSGTKLI

EAYTCTSVTVDSSGDIPVPMASGLPRVLLPASVVDSSSLCGGS*GSNSSTTTTTTATS*

*SSTATSKSASTSSTSTA*CTATSTSLAVTFEELVTTTYGEEIYLSGSISQLGDWDTSD

AVKMSADDYTSSNPEWSVTVTLPVGTTFEYKFIKVESDGTVTWESDPNREYTVPECG

SGETVVDTWR

A. niger alpha amylase expression cassette

US 8,927,250 B2

POLYPEPTIDES HAVING ALPHA-AMYLASE AND GRANULAR STARCH HYDROLYZING ACTIVITY

CROSS-REFERENCE TO RELATED APPLICATIONS

This application is a continuation application claiming priority to U.S. patent application Ser. No. 11/795,271, filed on Aug. 5, 2008, which is a 371 Patent Application of PCT/US2006/005622, filed on Feb. 17, 2006, now published as WO 2006/089107, on Aug. 24, 2006, which claimed priority to U.S. Provisional Application No. 60/654,105, filed on Feb. 18, 2005. The disclosures of the priority applications are incorporated herein by reference in their entirety.

SEQUENCE LISTING

The sequence listing submitted via EFS, in compliance with C.F.R. §1.52(e), is incorporated herein by reference. The sequence listing text file submitted via EFS contains the file "GC866-PCT_seqlist.txt", created on Nov. 3, 2011, which is 23,725 bytes in size.

FIELD OF THE INVENTION

The present invention relates to polypeptides having alpha-amylase activity and exhibiting granular starch hydrolyzing activity and biologically active fragments thereof, the heterologous expression of the polypeptides in host microorganisms as well as enzyme compositions comprising the polypeptides and uses of said polypeptides.

BACKGROUND OF THE INVENTION

Alpha-amylases (α-1,4-glucan-4-glucanohydrolase, EC 3.2.1.1.) hydrolyze internal α-1,4-glucosidic linkages in starch, largely at random to produce smaller molecular weight dextrins. These polypeptides are of considerable commercial value and are used in starch processing, in alcohol production, as cleaning agents, in the textile industry for starch desizing, in the paper and pulp industry, and in baking.

Alpha-amylases are produced by a wide variety of microorganisms including *Bacillus* and *Aspergillus*. Despite the advances made in the prior art concerning new and modified alpha-amylases there is a need in the art for alpha-amylases having a performance suitable for specific applications.

SUMMARY OF THE INVENTION

In a first aspect, the invention relates to an isolated polypeptide having alpha-amylase activity and granular starch hydrolyzing activity comprising an amino acid sequence which is at least 85% identical, preferably at least 90% identical or at least 95% identical or even at least 98% identical to SEQ ID NO: 8 and biologically active fragments thereof. The alpha amylase includes a catalytic domain, a linker and a starch-binding domain.

In some embodiments, the catalytic domain of the alpha-amylase has at least 95% sequence identity to SEQ ID NO: 5, the starch-binding domain has at least 80% sequence identity to SEQ ID NO: 7, and the linker has at least 90% sequence identity to SEQ ID NO: 6. In other embodiments, the alpha-amylase will comprise a signal sequence and preferably the signal sequence will have an amino acid sequence which is at least 90% identical to the sequence of SEQ ID NO: 4. In yet other embodiments, the alpha-amylase is obtained from an *Aspergillus niger* strain.

In a second aspect, the invention relates to a polynucleotide which encodes a polypeptide having alpha-amylase activity and granular starch hydrolyzing activity. In one embodiment, the polynucleotide encodes an alpha-amylase having at least 95% sequence identity with SEQ ID NO: 8. In other embodiments, the polynucleotide has the sequence of SEQ ID NO: 1 or SEQ ID NO: 2.

In a third aspect, the invention relates to a polypeptide having alpha-amylase activity comprising an amino acid sequence having at least 95% sequence identity to the sequence of SEQ ID NO: 5.

In a fourth aspect, the invention relates to a method of recombinantly producing an alpha-amylase having granular starch hydrolyzing activity comprising expressing a polynucleotide encoding a polypeptide having alpha-amylase activity in a filamentous fungal host cell, wherein the polypeptide comprises an amino acid sequence which is at least 85% identical, preferably 90% identical or at least 95% identical or even 98% identical to SEQ ID NO: 8 and comprises both a catalytic domain and a starch-binding domain. In some embodiments, the filamentous host cell is of the genus *Aspergillus*, such as *A. awamori, A. niger* or *A. oryzae*. In other embodiments, the filamentous host cell is of the genus *Trichoderma*, such as *T. reesei*.

In a fifth aspect, the invention relates to a filamentous fungal host cell comprising a heterologous polynucleotide encoding a polypeptide having alpha-amylase activity and granular starch hydrolyzing activity, the polypeptide comprising an amino acid which is at least 85% identical, preferably at least 90% identical or at least 95% identical or even 98% identical to SEQ ID NO: 8.

In a sixth aspect, the invention relates to an enzyme composition comprising a polypeptide having alpha-amylase activity and optionally having granular starch hydrolyzing activity, which comprises an amino acid sequence which is at least 85% identical, preferably at least 90% identical or at least 95% identical or even at least 98% identical to SEQ ID NO: 8 and biologically active fragments thereof. In one embodiment, of this aspect the amino acid sequence includes a catalytic domain, a linker and a starch-binding domain and in another embodiment of this aspect the amino acid sequence includes a catalytic domain.

In a seventh aspect, the invention relates to uses of the polypeptide of the invention having alpha-amylase activity and optionally granular starch hydrolyzing activity. Uses of the polypeptide in various processes include uses in starch conversion processes; processes for producing specialty syrups, processes for producing ethanol, and in fermentation processes for producing organic compounds, such as ascorbic acid, glutamic acid and glycerol.

BRIEF DESCRIPTION OF THE DRAWINGS

FIG. 1A-1B represent genomic DNA isolated from an *Aspergillus niger* (SEQ ID NO: 1), which encodes a polypeptide having alpha-amylase activity and granular starch hydrolyzing activity.

FIGS. 2A-2B represent the cDNA sequence (SEQ ID NO: 2) from the DNA sequence of FIG. 1, wherein 8 putative introns are removed.

FIG. 3 illustrates the translated alpha-amylase protein (SEQ ID NO: 3). The mature protein sequence, which excludes the signal sequence is represented by SEQ ID NO: 8). In the figure, the signal sequence is underlined (SEQ ID NO: 4); the catalytic domain is in bold (SEQ ID NO: 5); the linker region is in italics (SEQ ID NO: 6) and the starch-binding domain is double underlined (SEQ ID NO: 7).

DETAILED DESCRIPTION OF THE INVENTION

Figure 4:
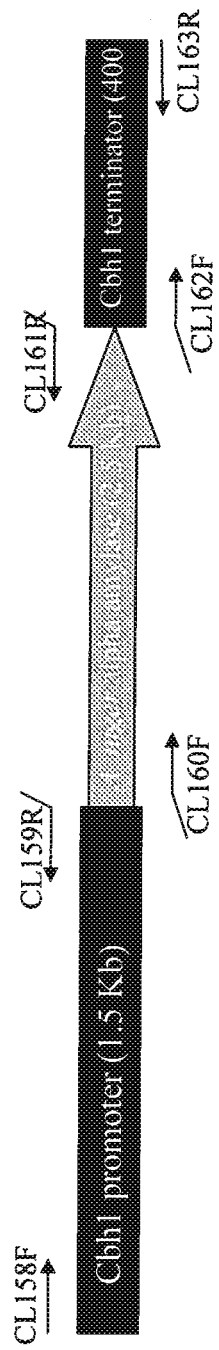
FIG. 4 illustrates the *A. niger* alpha-amylase expression cassette used in *Trichoderma reesei* transformation.

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). These general references provide definitions and methods known to those in the art. However, it is not intended that the present invention be limited to any particular methods, protocols, and reagents described, as these may vary.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, N.Y. (1991) provide one of skill with general dictionaries of many of the terms used in this invention.

Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole.
Definitions—

The term "alpha-amylase (e.g., E.C. class 3.2.1.1)" refers to polypeptides that catalyze the hydrolysis of alpha-1, 4-glucosidic linkages.

The term "acid-stable alpha amylase refers to an alpha-amylase that is active in the pH range of pH 3.0 to 7.0 and preferably 3.5 to 6.0.

The term "starch binding domain (SBD)" refers to a region of a polypeptide, which binds to a starch substrate.

The term "catalytic domain" refers to a structural region of a polypeptide which is distinct from the SBD and which contains the active site for substrate hydrolysis.

The term "linker" refers to a short amino acid sequence, which generally has between 3 and 40 amino acid residues, which covalently bind an amino acid sequence comprising a SBD with an amino acid sequence comprising a catalytic domain.

The term "granular starch" refers to raw (uncooked) starch, e.g., starch granules that have not been subject to temperatures that result in gelatinization.

A "biologically active fragment" means an amino acid fragment of an alpha-amylase encompassed by the invention, said fragment also having alpha-amylase activity.

The term "granular starch hydrolyzing (GSH) activity" refers to the ability of a polypeptide to hydrolyze starch in granular form.

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassaya, millet, potato, sweet potato, and tapioca.

The term "glucoamylase" refers to the amyloglucosidase class of enzymes (e.g., EC.3.2.1.3, glucoamylase, 1, 4-alpha-D-glucan glucohydrolase). These are exo-acting enzymes, which release glucosyl residues from the non-reducing ends of amylose and amylopectin molecules. The enzyme also hydrolyzes alpha-1, 6 and alpha-1,3 linkages although at much slower rate than alpha-1, 4 linkages.

Glucoamylase activity may be measured using the well-known assay which is based on the ability of glucoamylase to catalyze the hydrolysis of p-nitrophenyl-alpha-D-glucopyranoside (PNPG) to glucose and p-nitrophenol. At an alkaline pH, the nitrophenol; forms a yellow color that is proportional to glucoamylase activity and is monitored at 400 nm and compared against an enzyme standard measured as a GAU. In an embodiment, a "Glucoamylase Activity Unit" (GAU) is defined as the amount of enzyme that will produce 1 gm of reducing sugar, calculated as glucose per hour from a soluble starch substrate (4% ds) at pH 4.2 and 60° C.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "protein" and "polypeptide" are used interchangeably herein. The conventional one-letter or three-letter code for amino acid residues is used herein.

A "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

A "gene" refers to a DNA segment that is involved in producing a polypeptide and includes regions preceding and following the coding regions as well as intervening sequences (introns) between individual coding segments (exons).

The term "nucleic acid" encompasses DNA, cDNA, RNA, single stranded or double stranded and chemical modifications thereof. The terms "nucleic acid" and "polynucleotide" may be used interchangeably herein. The term cDNA refers to a DNA molecule which lacks the intron sequences that are usually present in the corresponding genomic DNA. A "coding" sequence is a nucleic acid sequence, which directly specifies the amino acid sequence of its protein product.

The term "heterologous" with reference to a polynucleotide or protein refers to a polynucleotide or protein that does not naturally occur in a host cell and includes a polynucleotide or polypeptide that has been introduced into a host cell by recombinant DNA technology. It is intended that the term encompass proteins that are encoded by naturally occurring genes, mutated genes, and/or synthetic genes.

The term "endogenous" with reference to a polynucleotide or protein refers to a polynucleotide or protein that occurs naturally in the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector.

A polynucleotide or a polypeptide having a certain percent (e.g. 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the GCG Pileup program, FASTA (Pearson et al. (1988) *Proc. Natl, Acad. Sci. USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al., (1997) *NAR* 25:3389-3402). Another preferred alignment program is ALIGN Plus (Scientific and Educational Software, PA), preferably using default parameters.

Another sequence software program that finds use is the TFASTA Data Searching Program available in the Sequence Software Package Version 6.0 (Genetics Computer Group, University of Wisconsin, Madison, Wis.).

One skilled in the art will recognize that sequences encompassed by the invention are also defined by the ability to hybridize under stringent hybridization conditions with an exemplified sequence (e.g., SEQ ID NO: 2). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1× SSC, 0.1% SDS.

"Host strain" or "host cell" means a host cell which is suitable for transformation with an expression vector or DNA construct. In one embodiment of the invention, "host cell" means both the cells and protoplasts created from the cells of a filamentous fungal strain.

The term "culturing" refers to growing a population of microbial cells under suitable conditions in a liquid or solid medium. In one embodiment, culturing refers to fermentative bioconversion of a starch substrate containing granular starch to an end-product (typically in a vessel or reactor). Fermentation is the enzymatic and anaerobic breakdown of organic substances by microorganisms to produce simpler organic compounds. While fermentation occurs under anaerobic conditions, it is not intended that the term be solely limited to strict anaerobic conditions, as fermentation also occurs in the presence of oxygen.

The phrase "simultaneous saccharification and fermentation (SSF)" refers to a process in the production of products in which a microbial organism, such as an ethanol producing microorganism and at least one enzyme such as a enzyme having alpha-amylase activity are in the same process step. In one embodiment of the present invention, SSF refers to the contemporaneous hydrolysis of granular starch substrates to saccharides including glucose and the fermentation of the saccharides into alcohol in the same reactor vessel.

The term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

The term "enzymatic conversion" in general refers to the modification of a substrate by enzyme action. The term as used herein also refers to the modification of a granular starch substrate by the action of an enzyme.

As used herein the term "saccharification" refers to enzymatic conversion of starch to glucose.

The term "gelatinization" means solubilization of a starch molecule by cooking to form a viscous suspension.

The term "liquefaction" refers to the stage in starch conversion in which gelatinized starch is hydrolyzed to give low molecular weight soluble dextrins.

The terms "end-product" or "desired end-product" refer to any carbon-source derived molecule product which is enzymatically converted from a starch containing substrate.

As used herein "ethanologenic microorganism" refers to a microorganism with the ability to convert sugars or oligosaccharides to ethanol. The ethanologenic microorganisms are ethanologenic by virtue of their ability to express one or more enzymes that individually or together convert sugar to ethanol.

As used herein the term "ethanol producer" or "ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Saccharomyces*, particularly, *S. cerevisiae*.

The terms "recovered", "isolated", and "separated" as used herein refer to a compound, protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein the term "specific activity" means an enzyme unit defined as the number of moles of substrate converted to product by an enzyme preparation per unit time under specific conditions. Specific activity is expressed as units (U)/mg of protein.

As used herein the term "enzyme unit" refers to the amount of enzyme that produces 1 micromole of product per minute under the specified conditions of the assay. In one embodiment, a granular starch hydrolyzing enzyme unit (GSHE U) is defined as being the amount of GSHE required to produce 1 mg of glucose per minute from granular starch under assay conditions of, for example 25° C. at pH 5.0. In an alternate embodiment, a GSHE U is defined as being the amount of a GSHE required to produce 1 mg glucose/min from a granular starch substrate at 50° C. at pH 4.5.

"ATCC" refers to American Type Culture Collection located at Manassas, Va. 20108 (ATCC; <www.atcc.org>).

"NRRL" refers to the Agricultural Research Service Culture Collection, National Center for Agricultural Utilization Research (and previously known as USDA Northern Regional Research Laboratory), Peoria, ILL.

"A", "an" and "the" include plural references unless the context clearly dictates otherwise.

As used herein the term "comprising" and its cognates are used in their inclusive sense; that is, equivalent to the term "including" and its corresponding cognates.

Polypeptides Having Alpha-amylase Activity.

In one embodiment, the present invention relates to a polypeptide having alpha-amylase activity. The polypeptide may also have granular starch hydrolyzing (GSH) activity. Alpha-amylase enzymes, E.C. class 3.2.1.1, have also been described as those effecting the exo- or endohydrolysis of 1,4-α-D-glucosidic linkages in polysaccharides containing 1,4-α-linked D-glucose units.

In some embodiments, the polypeptide having alpha-amylase activity comprises an amino acid sequence which is at least 85% identical, at least 90% identical, at least 95% identical, at least 96% identical, at least 97% identical, at least 98% identical and at least 99% identical to SEQ ID NO: 8. In some embodiments, the polypeptide will have the sequence of SEQ ID NO: 8. The polypeptide includes a catalytic domain, a linker and a starch-binding domain.

In some embodiments, the polypeptide having alpha-amylase activity and optionally granular starch hydrolyzing activity will differ from SEQ ID NO: 8 by including conservative amino acid replacements that do not significantly affect the activity of the polypeptide. Conservative replacements include, for example within the following groups a) acidic amino acids (Asp and Glu); b) basic amino acids (Arg, Lys and His); c) polar amino acids (Asn and Gln); d) aromatic amino acids (Phe, Tyr, Trp and His); and e) small amino acids (Ala, Ser and Gly). See, H. Neurath and R. L. Hill, 1979, THE PROTEINS, Academic Press, NY. Table 1 illustrates exemplary conservative amino acid substitutions that are recognized in the art. In addition substitution may be by one or more non-conservative amino acid substitutions, deletions, or insertions, which do not abolish the alpha amylase activity.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In some embodiments, the catalytic domain of the alpha-amylase will have at least 95%, at least 96%, at least 97%, at least 98% and at least 99% sequence identity to SEQ ID NO: 5. In other embodiments, the starch-binding domain will have at least 80%, at least 85%, at least 90%, at least 95%, at least 97%, at least 98% and at least 99% sequence identity to SEQ ID NO: 7. In further embodiments, the linker will have at least 90%, at least 95%, at least 96%, at least 97%, at least 98% and at least 99% sequence identity to SEQ ID NO: 6. In some embodiments, the linker will consistent of a sequence having 1, 2 or 3 amino acid residues more or less than the linker of SEQ ID NO: 6. In preferred embodiments, the polypeptides of the invention having alpha-amylase activity and optionally granular starch hydrolyzing activity are secreted proteins. In other embodiments, the polypeptides are acid-stable alpha-amylases.

In some embodiments, the alpha-amylase will comprise a signal sequence and preferably the signal sequence will comprise an amino acid sequence which is at least 90%, at least 95%, at least 96%, at least 97%, at least 98% and at least 99% identical to the sequence of SEQ ID NO: 4.

In some embodiments, the invention relates to biologically active fragments of an alpha-amylase encompassed by the invention, said fragments also having alpha-amylase activity. In some embodiments, biologically active fragments include alpha-amylases having at least 250 amino acid residues, at least 300 amino acid residues, at least 350 amino acid residues, at least 375 amino acid residues, and also at least 400 amino acid residues. In other embodiments, biologically active fragments include at least 60%, at least 70%, at least 80%, at least 85%, at least 90%, at least 93%, at least 95%, at least 97%, at least 98%, at least 99% of a polypeptide sequence having at least 95%, at least 97%, at least 98% and at least 99% sequence identity with the alpha-amylase having SEQ ID NO: 8.

Biologically active fragments of an alpha-amylase encompassed by the invention can be generated by methods known to those skilled in the art. The ability of a candidate fragment to exhibit a biological activity of an amylase can be assessed by methods known to those skilled in the art as described herein.

In some embodiments, the alpha-amylases of the invention, which include biologically active fragments, will comprise at least 20%, at least 30%, at least 40%, at least 50%, at least 60%, at least 70%, at least 80%, at least 90%, at least 95%, and at least 100% of the alpha-amylase activity of the mature polypeptide of SEQ ID NO: 8. In some embodiments, a biologically active fragment possesses at least 40% or at least 90% of the amylase activity of the alpha-amylase having SEQ ID NO: 8 in any in vivo or in vitro amylase activity assay.

In other embodiments, a polypeptide of the invention has at least 20%, at least 30%, at least 40%, at least 50%, at least 60%, at least 70%, at least 80% at least 90%, at least 95% and preferably at least 100% of the granular starch hydrolyzing activity of the mature polypeptide of SEQ ID NO: 8.

In yet other embodiments, a polypeptide of the present invention is a wild-type alpha-amylase identified and isolated from a filamentous fungus. The polypeptide of the present invention is preferably isolated from an *Aspergillus* strain such as an *Aspergillus niger* strain. Further, the polypeptide of the invention may be prepared by techniques known in the art.

Polynucleotides Encoding the Alpha-amylase of the Invention.

In another embodiment, the invention is relates to isolated polynucleotides which encode a polypetide of the invention having alpha-amylase activity and optionally granular starch hydrolyzing activity (GSH). In a preferred embodiment, the polynucleotide is set forth in SEQ ID NO: 1 or SEQ ID NO: 2. In other preferred embodiments, the polynucleotide has a sequence which is at least 80%, at least 85%, at least 90%, at least 95%, at least 96%, at least 97%, at least 98% and at least 99% identical to SEQ ID NO: 1 or SEQ ID NO: 2. In some preferred embodiments, the polynucleotide will encode a polypeptide having alpha-amylase activity and GSH activity comprising a polypeptide sequence having at least 90% sequence identity to SEQ ID NO: 8.

In other embodiments, the polynucleotide will encode a biologically active fragment having alpha-amylase activity. In some embodiments, the polynucleotide will encode a catalytic domain of an alpha-amylase encompassed by the invention. In some preferred embodiments, the polynucleotide will encode a biologically active fragment which has at least 95% sequence identity to the sequence having SEQ ID NO: 5.

One skilled in the art is well aware of the degeneracy of the genetic code and because of this degeneracy, more than one codon can be used to encode a particular polypeptide. The present invention encompasses polynucleotides which encode a particular amino acid sequence.

Techniques used to isolate or clone a polynucleotide encoding a polypeptide are known in the art and include isolation of genomic DNA, preparation from cDNA or a combination thereof. Additionally amplification techniques such as the polymerase chain reaction (PCR) using specific primers, ligase chain reaction (LCR), ligated activated transcription (LAT), nucleic acid sequence based amplification (NASBA) and antibody screening of expression libraries to detect cloned DNA may be used. (See, e.g. Innis et al., 1990, PCR: A GUIDE TO METHODS AND APPLICATIONS, Academic Press NY). Further, a polynucleotide sequence encoding a polypeptide of the invention may be prepared synthetically by established techniques.

Expression of an Alpha-amylase of the Invention.

According to the invention, a DNA sequence encoding a polypetide having alpha-amylase activity and optionally granular starch hydrolyzing activity as described above can be expressed in enzyme form using a DNA construct (expression vector) which typically includes a promoter, signal sequence, and optionally other control sequences. Nucleic acid constructs and expression vectors—

In a further embodiment, the invention relates to nucleic acid constructs comprising a polynucleotide encoding a polypeptide having alpha-amylase activity and optionally granular starch hydrolyzing activity operably linked to a suitable promoter, which shows transcriptional activity in a host cell (e.g. a fungal host cell).

The promoter may be derived from genes encoding proteins either homologous or heterologous to the host cell. The promoter may be a truncated or hybrid promoter. Preferably, the promoter is useful in a *Trichoderma* host or an *Aspergillus* host.

Suitable nonlimiting examples of promoters include cbh1, cbh2, egl1, egl2. In one embodiment, the promoter is one that is native to the host cell. For example, when *T. reesei* is the host, the promoter is a native *T. reesei* promoter. In one embodiment, the promoter is *T. reesei* cbh1, which is an inducible promoter and has been deposited in GenBank under Accession No. D86235. An "inducible promoter" is a promoter that is active under environmental or developmental regulation. In another embodiment, the promoter is one that is heterologous to the fungal host cell. Other examples of useful promoters include promoters from the genes of *A. awamori* and *A. niger* glucoamylase genes (glaA) (Nunberg et al., (1984) *Mol. Cell. Biol.* 4:2306-2315 and Boel et al., (1984) *EMBO J.* 3:1581-1585); *Aspergillus oryzae* TAKA amylase; *Rhizomucor miehei* aspartic proteinase; *Aspergillus niger* neutral alpha-amylase; *Aspergillus niger* acid stable alpha-amylase; *Trichoderma reesei* xln1 and the cellobiohydrolase 1 gene promoter (EPA 137280A1) and mutant, truncated and hybrid promoters thereof.

In some embodiments, the DNA construct or expression vector includes a termination sequence. The terminator sequence is operably linked to the 3' terminus of the nucleic acid sequence encoding the polypeptide. Any terminator functional in the host cell may be used. In one embodiment, the termination sequence and the promoter sequence are derived from the same source. In another embodiment, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase (Nunberg et al. (1984) supra, and Boel et al., (1984) supra); *Aspergillus nidulans* anthranilate synthase; *Aspergillus niger* alpha-glucosidase and *Aspergillus oryzae* TAKA amylase.

In some embodiments, the polypeptide coding sequence is operably linked to a signal sequence which directs the encoded polypeptide into the cell's secretory pathway. The 5' end of the coding sequence may naturally contain a signal sequence naturally linked in translation reading frame with the segment of the coding region which encodes the secreted polypeptide. The DNA encoding the signal sequence is preferably that which is naturally associated with the polypeptide to be expressed. Preferably, the signal sequence is encoded by an *Aspergillus niger* alpha-amylase, *Aspergillus niger* neutral amylase or *Aspergillus niger* glucoamylase. In some embodiments, the signal sequence is the *Trichoderma* cdh1 signal sequence which is operably linked to a cdh1 promoter. More preferably, the signal sequence has at least 90%, at least 95%, at least 97%, at least 98% and at least 99% sequence identity to the signal sequence of SEQ ID NO: 4. In additional embodiments, a signal sequence and a promoter sequence comprising a DNA construct or vector to be introduced into a fungal host cell are derived from the same source.

In some embodiments, the DNA construct or expression vector may include polyadenylation sequences for filamentous fungal host cells which may be obtained for example from *Aspergillus oryzae* TAKA amylase, *Aspergillus niger* glucoamylase, *Aspergillus nidulans*, *Aspergillus niger* alpha glucosidase and *Aspergillus niger* alpha amylase.

In some embodiments, a DNA construct or an expression vector includes a selectable marker. Examples of preferred selectable markers include ones which confer antimicrobial resistance (e.g., hygromycin, chloramphenicol and phleomycin). Nutritional and metabolic selective markers also find use in the present invention including those markers known in the art as amdS argB and pyr4.

Markers useful in vector systems for transformation of for example *Trichoderma* are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6.; and Kinghorn et al. (1992) APPLIED MOLECULAR GENETICS OF FILAMENTOUS FUNGI, Blackie Academic and Professional, Chapman and Hall, London). In one embodiment, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475-479 and Penttila et al., (1987) *Gene* 61:155-164. Also useful are pyrG genes of *A. nidulans* and *A. oryzae*.

An expression vector comprising a DNA construct with a polynucleotide encoding a polypeptide having alpha-amylase activity and optionally having GSH activity according to the invention may be any vector which is capable of replicating autonomously in a given fungal host organism or of integrating into the DNA of the host. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press pp. 396-428 and U.S. Pat. No. 5,874,276. Particularly useful vectors include pFB6, pBR322, PUC18, pUC100 and pENTR/D.

In some embodiments, the expression vector is a plasmid. In some embodiments, two types of expression vectors for obtaining expression of genes are contemplated.

The first expression vector comprises DNA sequences in which the promoter, polypeptide coding region, and terminator all originate from the gene to be expressed. In some embodiments, gene truncation is obtained by deleting undesired DNA sequences (e.g., DNA encoding unwanted domains) to leave the domain to be expressed under control of its own transcriptional and translational regulatory sequences.

The second type of expression vector is preassembled and contains sequences required for high-level transcription and a selectable marker. In some embodiments, the coding region for an alpha-amylase or part thereof is inserted into this general-purpose expression vector such that it is under the transcriptional control of the expression construct promoter and terminator sequences. In some embodiments, genes or part thereof are inserted downstream of a strong promoter such as the cbh1 promoter.

Methods used to ligate the DNA construct comprising a polynucleotide encoding an alpha-amylase, a promoter, a terminator and other sequences and to insert them into a suitable vector are well known in the art. Linking is generally accomplished by ligation at convenient restriction sites. If such sites do not exist, the synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Host Cells—

Host cells include those cells in which expression of an alpha-amylase according to the present invention can be achieved. Host cells are transformed or transfected with vectors constructed using recombinant DNA techniques. In some embodiments, the host cell is a strain of *E. coli*, *Pseudomonas*, *Bacillus*, *Streptomyces*, various fungi and yeast. Some preferred host cells include fungal cells, particularly filamentous fungal cells.

The term "filamentous fungi" refers to all filamentous forms of the subdivision Eumycotina (See, Alexopoulos, C. J. (1962), INTRODUCTORY MYCOLOGY, Wiley, N.Y.). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

The filamentous fungal cell may be a cell of a species of, but not limited to, *Trichoderma* sp. (e.g., *Trichoderma reesei* (previously classified as *T. longibrachiatum* and currently also known as *Hypocrea jecorina*), *Trichoderma viride*, *Trichoderma koningii*, and *Trichoderma harzianums*)); *Penicillium* sp., *Humicola* sp. (e.g., *Humicola insolens* and *Humicola grisea*); *Chrysosporium* sp. (e.g., *C. lucknowense*); *Gliocladium* sp., *Aspergillus* sp. (e.g., *A. oryzae*, *A. niger*, *A. awamori*, *A. nidulans*, *A. aculeatus* and reference is made to in Ward et al. (1993) Appl. Microbiol. Biotechnol. 39:738-743 and Goedegebuur et al., (2002) Curr Gene 41:89-98.)), *Fusarium* sp. (e.g. *F. bactridiodes*, *F. cerealis*, *F. graminearum*, *F. oxysporum*, and *F. roseum*), *Mucor* sp. (e.g. *M. miehei*), *Neurospora* sp. (e.g. *N. crassa*), *Sclerotium* (*Athelia*) sp. (e.g., *A. rolfii*), *Hypocrea* sp., and *Emericella* sp. (See also, Innis et al., (1985) Sci. 228:21-26).

As used herein, the term "*Trichoderma*" or "*Trichoderma* sp." refer to any fungal genus previously or currently classified as *Trichoderma*. In some embodiments, particular strains of *Trichoderma reesei* include ATCC No. 13631, ATCC No.

26921, ATCC No. 56764, ATCC No. 56765, ATCC No. 56767 and NRRL 15709. In some preferred embodiments, the host strain is a derivative of RL-P37. RL-P37 is disclosed in Sheir-Neiss et al. (1984) Appl. Microbiol. Biotechnology 20:46-53.

In some embodiments, the host cell is a member of the genus *Bacillus*, while in some embodiments, the *Bacillus* strain of interest in an industrial *Bacillus* strain. Examples of industrial *Bacillus* strains include, but are not limited to *B. licheniformis, B. subtilis, B lentus, B amyloliquefaciens*. In additional embodiments, the *Bacillus* host strain is selected from the group consisting of *B. lentus, B. brevis, B. stearothermophilus, B. alkalophilus, B. coagulans, B. cirulans, B. pumilus, B. thuringiensis, B. clausii,* and *B. megaterium*, as well as other organisms within the genus *Bacillus*. In some preferred embodiments, *B. subtilis* or *B. licheniformis* is used. For example, U.S. Pat. Nos. 5,264,366 and 4,760,025 (RE34, 606), and US2002/0182734 (International Publication No. WO 02/14490) describe various *Bacillus* host strains that find use in the present invention.

In some embodiments, native genes will be deleted or inactivated in the host cell, for example the strain may be an alpha-amylase negative *Bacillus* strain (genes deleted); an alpha-amylase and protease deleted *Bacillus* strain (ΔamyE, Δapr, Δnpr) or a *Trichoderma* strain with one or more genes deleted (e.g., Δcbh1, Δcbh2, Δegl1, and Δegl2). See, for example, U.S. Pat. No. 5,847,276 and WO 05/001036. Methods for making gene deletions are known in the art and reference is made to U.S. Pat. No. 5,246,853, U.S. Pat. No. 5,475,101 and WO 92/06209.

Methods of Transformation—

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. No. 6,022,725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Methods of transformation of *Aspergillus* are described in Yelton, Hamer and Timberlake, (1984) Proc. Natl. Acad. Sci. USA 81: 1470-1474 and Cao et al., (2000) *Sci.* 9:991-1001; for *Fusarium* in Bajar, Podila and Kolattukudy, (1991) Proc. Natl. Acad. Sci. USA 88: 8202-8212, and for *Streptomyces* include Hopwood et al., 1985, Genetic Manipulation of *Streptomyces*: Laboratory Manual, The John Innes Foundation, Norwich, UK and Fernandez-Abalos et al., Microbiol 149:1623-1632 (2003) and for *Bacillus* include Brigidi, DeRossi, Bertarini, Riccardi and Matteuzzi, (1990) FEMS Microbiol. Lett. 55: 135-138.

Preferably, genetically stable transformants are constructed with vector systems whereby the nucleic acid encoding an alpha-amylase is stably integrated into a host strain chromosome. Transformants are then purified by known techniques.

In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

In one specific embodiment, the preparation of *Trichoderma* sp. for transformation involves the preparation of protoplasts from fungal mycelia. (See, Campbell et al., (1989) *Curr. Genet.* 16:53-56). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like.

Uptake of DNA into the host *Trichoderma* sp. strain is dependent upon the calcium ion concentration. Generally, between about 10 mM $CaCl_2$ and 50 mM $CaCl_2$ is used in an uptake solution. Besides the need for the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG).

Usually a suspension containing the *Trichoderma* sp. protoplasts or cells that have been subjected to a permeability treatment at a density of $10^5$ to $10^7$/mL are used in transformation. A volume of 100 μL, of these protoplasts or cells in an appropriate solution (e.g., 1.2 M sorbitol; 50 mM $CaCl_2$) are mixed with the desired DNA. Generally, a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. (See, e.g., U.S. Pat. Nos. 6,022,725 and 6,268,328, both of which are incorporated by reference).

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only.

Cell Culture—

Generally, cells are cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) also find use in the present invention.

Culture conditions are also standard, (e.g., cultures are incubated at approximately 28° C. in appropriate medium in shake cultures or fermenters until desired levels of alpha-amylase expression are achieved). Preferred culture conditions for a given host, such as a filamentous fungus, are known in the art and may be found in the scientific literature and/or from sources such as the American Type Culture Collection and Fungal Genetics Stock Center.

After host cell growth (e.g. fungal growth) has been established, the cells are exposed to conditions effective to cause or permit the expression of an alpha-amylase as defined herein. In cases where the coding sequence of an alpha-amylase is under the control of an inducible promoter, the inducing agent (e.g., a sugar, metal salt or antimicrobial), is added to the medium at a concentration effective to induce alpha-amylase expression.

In some embodiments of the present invention, host cells (e.g., fungal cells) expressing an alpha-amylase of the invention are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

Alpha-amylase Production.

The invention relates to methods of producing a polypeptide of the invention comprising culturing a host cell which is capable of producing a polypeptide having alpha-amylase activity encompassed by the invention and recovering the polypeptide, Preferably the host cell is a *Bacillus* cell; an *Aspergillus* cell (e.g. an *Aspergillus niger* cell) or a *Trichoderma* cell (e.g., a *Trichoderma reesei* cell).

The invention further relates to methods of recombinantly producing a polypeptide having alpha-amylase activity and optionally granular starch hydrolyzing activity in a host cell comprising culturing a host cell under suitable culture conditions for the production of the alpha-amylase and recovering the alpha-amylase. In some preferred embodiments, the host cell is a filamentous fungal host cell is an *Aspergillus* cell and in other preferred embodiments, the filamentous fungal host cell is a *Trichoderma* cell.

Identification of Alpha-amylase Activity and GSH Activity.

To evaluate the expression of an alpha-amylase by a cell line, assays can be carried out at the protein level, the RNA level or by use of functional bioassays particular to alpha amylase activity and/or production. In general assays employed include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of an alpha-amylase may be measured in a sample directly, for example, by assays directly measuring reducing sugars such as glucose in the culture media and by assays for measuring glucoamylase activity, expression and/or production.

Further, gene expression may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of an alpha-amylase. The details of such methods are known to those of skill in the art and many reagents for practicing such methods are commercially available.

Alpha-amylase activity may be measured for example by using the DNS method as described in Miller, G. L. (1959) *Anal. Chem.* 31:426-428. Alternative methods using kits may also be used.

Substrates useful for assaying GSH activity include granular starch substrates such as corn starch, wheat starch, rice starch, and milo starch. For example, glucose concentration may be determined by any convenient method such as by using glucose reagent kit No 15-UV (Sigma Chemical Co.) or an instrument such as Technicon Autoanalyzer. Also reference is made to glucose oxidase kits and glucose hexose kits commercially available from Instrumentation Lab. (Lexington, Mass.).

To determine the affinity of the starch binding domain to granular starch substrates the method described in Belshaw & Williams, 1990 FEBS Lett. 269:350-353 may be used wherein various amount of the starch binding domain are incubated with the granular cornstarch in a buffer. The reaction is terminated by centrifugation and the protein concentration of the supernatant is determined and subtracted from the total protein to give the amount of starch bound protein.

In some embodiments of the invention, the polypeptides having alpha-amylase activity and optionally granular starch hydrolyzing activity expressed in a *Trichoderma* or *Aspergillus* host will be greater than 1 gram protein per liter (g/L), greater than 2 g/L, greater than 5 g/L, greater than 10 g/L, greater than 20 g/L, greater than 25 g/L, greater than 30 g/L, greater than 50 g/L and also greater than 100 g/L of culture media.

Methods for Recovering Alpha-amylase.

In general, the alpha-amylase produced in cell culture is secreted into the medium and may be purified or isolated, e.g., by removing unwanted components from the cell culture medium. In some cases, an alpha-amylase may be produced in a cellular form necessitating recovery from a cell lysate. In such cases the enzyme is purified from the cells in which it was produced using techniques routinely employed by those of skill in the art. Examples include, but are not limited to, affinity chromatography (Tilbeurgh et al., (1984) *FEBS Lett.* 16:215); ion-exchange chromatographic methods (Goyal et al., (1991) *Biores. Technol.* 36:37; Fliess et al., (1983) *Eur. J. Appl. Microbiol. Biotechnol.* 17:314; Bhikhabhai et al., (1984) *J. Appl. Biochem.* 6:336; and Ellouz et al., (1987) *Chromatography* 396:307), including ion-exchange using materials with high resolution power (Medve et al., (1998) *J. Chromatography A* 808:153; hydrophobic interaction chromatography (Tomaz and Queiroz, (1999) *J. Chromatography A* 865:123; two-phase partitioning (Brumbauer, et al., (1999) *Bioseparation* 7:287); ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75.

Enzyme Compositions.

In some aspects, the invention relates to enzyme compositions, which comprise the polypeptides of the invention having alpha-amylase activity and optionally granular starch hydrolyzing activity.

In some embodiments, the alpha-amylase is available as a cell free filtrate (for example wherein the alpha-amylase is isolated from a culture medium), and in other embodiments, the alpha-amylase is available in a culture medium containing the fungal host cells which express and secrete the alpha-amylase.

Enzyme compositions include compositions for starch conversion, compositions for granular starch hydrolysis, cleaning compositions, such as detergent, hard surface cleaning and dishwashing compositions, compositions for paper and pulp production, textile treatment compositions, brewing compositions, baking compositions, animal feed compositions, alcohol fermentation compositions and compositions for the production of sweeteners.

As understood by those in the art, the quantity of alpha-amylase used in the compositions and methods of the present invention will depend on the enzymatic activity of the alpha-amylase and the use of the composition. In some embodiments, the range of alpha-amylase present in an enzyme composition is from 0.001 to 15.0 SSU per gram of dry solids content of a slurry comprising a substrate contain granular starch.

Depending on the specific composition, one or more additional enzymes may be included. Non-limiting examples of these enzymes include a second amylase, such as a beta-amylase or maltogenic alpha-amylase; glucoamylases, proteases, cellulases, lipases, cutinases, esterases, hemicellulases, laccases, mannanases, cyclodextrin glucanotransferases, pullulanases, oxidoreductases and glycosyltransferases. These enzymes may be obtained from fungal, bacterium or plant sources.

Industrial Applications and Uses

Alpha-amylases are of considerable commercial value and the alpha-amylases of the invention may be used in starch processing, in alcohol production, as cleaning agents, in the sweetener industry, in the textile industry for starch desizing, in the paper and pulp industry and in baking applications.

In one preferred embodiment, an alpha-amylase of the invention is used for starch processing particularly for alcohol fermentation, such as for fuel or portable ethanol. The alpha-amylases encompassed by the invention may be used in various process steps including pretreatment, liquefaction and saccharification steps.

In some embodiments, the alpha-amylase of the invention may be used in a process for hydrolyzing granular starch from a granular starch substrate, such as cornstarch, at a temperature below the gelatinization temperature of the granular starch in the substrate. The granular starch to be used in the process may be highly refined starch or it may be a more crude starch containing milled whole grain. In some embodiments, the temperature of the starch hydrolysis process will be conducted in the range of 25° C. to 70° C. In other embodiments, the temperature will be in greater than 30° C. but less than 70° C., less than 68° C., less than 65° C., less than 60° C., less than 55° C., less than 50° C., and less than 45° C. In some embodiments, the alpha-amylase according to the invention may be used in a method for liquefying starch.

In some embodiments, the fermentation may be carried out sequentially to the hydrolysis of the starch containing substrates and in other embodiments the fermentation may be carried out simultaneously with the hydrolysis in a process known as simultaneous saccharification and fermentation (SSF). During SSF a starch containing substrate, generally in slurry form, is contacted simultaneously with an alpha-amylase of the invention and ethanol producing microorganisms to produce alcohol or other useful compounds.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the disclosure and experimental section which follows, the following abbreviations apply:

wt % (weight percent); ° C. (degrees Centigrade); rpm (revolutions per minute); $H_2O$ (water); $dH_2O$ (deionized water); $dIH_2O$ (deionized water, Milli-Q filtration); aa (amino acid); by (base pair); kb (kilobase pair); kD (kilodaltons); g or gm (grams); μg (micrograms); mg (milligrams); μL (microliters); ml and mL (milliliters); mm (millimeters); μm (micrometer); M (molar); mM (millimolar); μM (micromolar); U (units); V (volts); MW (molecular weight); sec (seconds); min(s) (minute/minutes); hr(s) (hour/hours); PAGE (polyacrylamide gel electrophoresis); DO (dissolved oxygen); phthalate buffer (sodium phthalate in water, 20 mM, pH 5.0); PBS (phosphate buffered saline [150 mM NaCl, 10 mM sodium phosphate buffer, pH 7.2]); SDS (sodium dodecyl sulfate); Tris (tris (hydroxymethyl)aminomethane); w/v (weight to volume); w/w (weight to weight); v/v (volume to volume); Genencor (Genencor International, Inc., Palo Alto, Calif.).

The following assays and methods are contemplated for use in the examples provided below:

Alpha-amylase activity: The measurement of alpha-amylase activity is based on the degree of hydrolysis of soluble potato starch substrate (4% ds) by an aliquot of the enzyme sample at pH 4.5, 50° C. The reducing sugar content is measured using the DNS method as described in Miller, G. L. (1959) *Anal. Chem.* 31:426-428. One unit of the enzyme activity (SSU, soluble starch unit) is equivalent to the reducing power of 1 mg of glucose released per minute at the specific incubation conditions.

Determination of total starch content: The enzyme-enzyme starch liquefaction and saccharification process is used to determine the total starch content. In a typical analysis, 2 g of the dry sample is taken in a 100 ml Kohlraucsh flask and 45 ml of MOPS buffer, pH 7.0 is added. The slurry is well stirred for 30 min. An alpha-amylase e.g. SPEZYME FRED (1:50 diluted in water), 1.0 ml is added and heated to boiling for 3-5 min. The flask is placed in an autoclave maintained at 121° C. for 15 min. After autoclaving the flask is placed in a water bath at 95° C. and 1 ml of the 1:50 diluted SPEZYME FRED is added and incubated for 45 min. The pH is adjusted to pH 4.2 and the temperature is reduced to 60° C. This is followed by addition of 20 ml acetate buffer, pH 4.2. Saccharification is carried out by adding 1.0 ml of 1:100 diluted OPTIDEX L-400 (Glucoamylase from Genencor International Inc.) and the incubation is continued for 18 hr at 60° C. The enzyme reaction is terminated by heating at 95° C. for 10 min. The total sugar composition is determined by HPLC analysis using glucose as a standard. The soluble starch hydrolysate from water extraction of a sample at room temperature without enzymatic treatment is subtracted from the total sugar.

Residual starch iodine test: A sample of the fermentation broth is centrifuged in 2 ml plastic centrifuge tubes. The supernatant is decanted and the tube containing the pellet is placed in an ice bath. Several drops of 0.025N iodine solution (0.1N iodine from VWR Cat. No. VW3207-1 diluted 4×) is added to the pellet and mixed. A positive (+) starch shows a range of color from blue to purple and the intensity of color is directly proportional to the concentration of starch. A negative result (−) remains yellowish.

Total protein analysis: The total nitrogen (N) in the sample preparations is determined using the Kjeldhal method (American Assoc. Cereal Chemists (AACC), (1983), Methods 22B60 8th Ed. St Paul, Minn.). Protein content is calculated by 6.25× total N.

Ethanol and carbohydrate determinations—Ethanol and carbohydrate composition of the samples are determined using the HPLC method as described herein:

a) a 1.5 mL Eppendorf centrifuge tube is filled with fermentor broth and cooled on ice for 10 min;
b) the sample tube is centrifuged for 1 min in Eppendorf table top centrifuge;
c) a 0.5 mL sample of the supernatant is transferred to a test tube containing 0.05 mL of Kill solution (1.1N $H_2SO_4$) and allowed to stand for 5 min;
d) 5.0 mL of water is added to the test tube sample and then filtered into a HPLC vial through 0.45 μm Nylon Syringe Filter; and
e) run on HPLC.

HPLC Conditions:
a) Ethanol System: Column: Phenomenex Rezex Organic Acid Column (RHM-Monosaccharide) #00H-132 KO (Equivalent to Bio-Rad 87H); Column Temperature: 60° C.; Mobile Phase: 0.01 N $H_2SO_4$; Flow Rate: 0.6 mL/min Detector: RI; Injection Volume: 20 μL b) Carbohydrate System: Column: Phenomenex Rezex Carbohydrate (RCM-Monosaccharide) #00H-0130-KO (Equivalent to Bio-Rad 87H); Column Temperature: 70° C.; Mobile Phase: Nanopure DI $H_2O$; Flow Rate: 0.8 mL/min Detector: RI; Injection Volume: 10 μL (3% DS material);

The column separates based on the molecular weight of the saccharides, which are designated as DP1 (monosaccharides); DP2 (disaccharides); DP3 (trisaccharides) and DP+4 (oligosaccharide sugars having a degree of polymerization greater than 3).

EXAMPLE 1

Cloning the *Aspergillus niger* Alpha-amylase Gene

Genomic DNA was extracted from frozen *A. niger* (NRRL 3, ATCC 9029) mycelia. The frozen mycelia were ground with dry ice in a coffee grinder and the DNA was extracted by the EasyDNA protocol (Invitrogen). An extra chloroform/phenol/isoamyl alcohol extraction was added to the standard protocol. PCR primers were designed, based on homology of alpha-amylase sequences to contigs in an *A. niger* strain NRRL 3 shotgun sequencing genomic DNA database (purchased from Integrated Genomics). The forward primer contained a motif for directional cloning into a Gateway entry vector (Invitrogen).

```
                                          (SEQ ID NO: 9)
Forward primer, Anaa5: CAC CAT GAG ACT ATC GAC TTC AAG
and
                                          (SEQ ID NO: 10)
reverse primer, Anaa4b: TTA CCT CCA AGT GTC AAC

CAC CGT CTC.
```

The PCR product (using Pfu Turbo DNA polymerase, Stratagene) included multiple bands. The largest band, 2.4 kb, was purified by gel extraction (QIAquick Gel Extraction Kit, Qiagen). The PCR product was cloned into pCR_BluntII_TOPO (Zero Blunt TOPO PCR Cloning Kit, Invitrogen) for sequencing. The vector, pCR_BluntII_9029alpha, was transformed into chemically competent Top10 *E. coli* (Invitrogen) with kanamycin selection. Plasmid DNA from several clones was digested with EcoRI to confirm the correct size insert. The alpha-amylase insert was sequenced (Sequetech, Mountain View, Calif.) (FIGS. 1-3). The new alpha-amylase (2365 bp) showed sequence homology with known *Aspergillus* alpha-amylases, having more identity in the exons and less identity in the 8 introns.

EXAMPLE 2

Construction of an Expression Cassette

The following procedures were used in constructing an expression cassette, which includes a polynucleotide encoding the alpha-amylase of the invention. The alpha amylase DNA sequence in vector pCR_BluntII_9029alpha was transferred to an expression cassette (FIG. 4) by fusion PCR. In the first step, three fragments of DNA were individually PCR amplified using the following primers:

For the *T. reesei* cbh1 promoter region (1.49 kb fragment size)

CL158F (SEQ ID NO: 11)
5' TAGAGTTGTGAAGTCGGTAATCCCGC 3'
and

CL159R (SEQ ID NO: 12)
5' CGATAGTCTCATTGACTATTGGGTTTCTGTGCCTC 3';

for the *A. niger* alpha-amylase region (2.37 kb fragment size)

CL160F (SEQ ID NO: 13)
5' ACCCAATAGTCAATGAGACTATCGACTTCAAG 3'
and

CL161R (SEQ ID NO: 14)
5' TCGCACGGAGCTTTACCTCCAAGTGTCAACCACCGTCTC 3';

for the *T. reesei* cbh1 terminator region (0.35 kb fragment size)

CL162F (SEQ ID NO: 15)
5' TTGGAGGTAAAGCTCCGTGCGAAAGCCTGAC 3'
and

CL163R (SEQ ID NO: 16)
5' TACTGGGATACACGAAGAGCGG 3'

Cbh1 promoter and terminator regions were amplified from *T. reesei* genomic DNA (extracted from strain *T. reesei* QM6a, ATCC number 13631). *A. niger* alpha-amylase was amplified using the vector-pCR_BluntII_9029alpha as template. Pfu Ultra DNA polymerase (Stratagene) was used for amplification. After performing PCR, the individual reactions were run through agarose gels and the appropriately sized fragments were excised and purified (QIAquick Gel Extraction Kit, Qiagen).

Next a fusion PCR reaction was performed to join the three fragments into a single expression cassette fragment of the form: cbh1 promoter linked to the *A. niger* alpha-amylase linked to the cbh1 terminator (FIG. 4). Approximately equimolar amounts of each of the three fragments was included in the PCR fusion reaction along with the primers:

(SEQ ID NO 17)
596F 5' GTGAAGTCGGTAATCCCGCTGTATAG 3'

(SEQ ID NO: 18)
597R 5' GGATACACGAAGAGCGGCGATTC 3'

Herculase DNA polymerase (Stratagene) was used according to the manufacture's instructions. The following PCR cycle program was used on a PTC-200 Thermocycler (MJ Research): Step 1—95° C. for 2'; step 2—95° C. for 30"; step 3—55° C. for 30"; step 4—72° C. for 5'; step 5—go to step 2 for 9 cycles; step 6—95° C. for 30"; step 7—55° C. for 30"; step 8—72° C. for 5' add 10" per cycle; step 9—go to step 6 for 19 cycles; step 10—72° C. for 10'; step 11—4° C. hold at this temperature; and step 12 end.

A 4.17 kb DNA fragment was amplified and purified from agarose gel (QIAquick Gel Extraction Kit, Qiagen). Additionally other non-specific reaction products were formed (two prominent fragments were sized 1.7 and 2.0 kb). These non-specific products were discarded.

The fungal selectable marker, *Aspergillus nidulans* amdS gene, including its promoter and terminator, was isolated by restriction digest and purified from agarose from a vector equivalent to p3SR2 (Hynes et al., (1983) *Mol. Cell. Biol.* 3:1430-1439). The *A. nidulans* amdS gene is further referenced in NCBI Genebank record M16371).

EXAMPLE 3

Co-Transformation and Fermentation of *Trichoderma reesei*

Biolistic transformation of *T. reesei* with the *A. niger* alpha-amylase expression construction and the *A. nidulans* amdS marker was performed using the protocol outlined below.

A suspension of spores (approximately $3.5 \times 10^8$ spores/ml) from a quad deleted strain of *T. reesei* (WO 05/001036) was prepared. 100 ul-200 ul of spore suspension was spread onto the center of plates of MM acetamide medium. MM acetamide medium had the following composition: 0.6 g/L acetamide; 1.68 g/L CsCl; 20 g/L glucose; 20 g/L $KH_2PO_4$; 0.6 g/L $CaCl_2.2H_2O$; 1 ml/L 1000× trace elements solution; 20 g/L Noble agar; pH 5.5. 1000× trace elements solution contained 5.0 g/l $FeSO_4.7H_2O$, 1.6 g/l $MnSO_4.H_2O$, 1.4 g/l $ZnSO_4.7H_2O$ and 1.0 g/l $CoCl_2.6H_2O$. The spore suspension was allowed to dry on the surface of the MM acetamide medium.

Transformation of *T. reesei* was performed using a Biolistic® PDS-1000/He Particle Delivery System from Bio-Rad (Hercules, Calif.) following the manufacturer's instructions. Briefly, 60 mg of M10 tungsten particles were placed in a microcentrifuge tube. 1 mL of ethanol was added, the mixture was briefly vortexed and allowed to stand for 15 minutes. The particles were centrifuged at 15,000 rpm for 15 minutes. The ethanol was removed and the particles were washed three times with sterile $dH_2O$ before 1 mL of 50% (v/v) sterile glycerol was added. After ten seconds of vortexing, 25 ul of tungsten/glycerol particle suspension was removed and placed into a microcentrifuge tube. While continuously vortexing the 25 ul tungsten/glycerol particle suspension, the following were added; in order, allowing 5' incubations between additions; 2 ul (50-100 ng/ul) of *A. nidulans* amdS marker DNA, 2-3 ul *A. niger* alpha-amylase construct (50-100 ng/ul) DNA, 25 ul of 2.5M $CaCl_2$ and 10 ul of 0.1M spermidine. After another 5' incubation after spermidine addition, the particles were centrifuged for 3 seconds. The supernatant was removed; the particles were washed with 200 ul of 70% (v/v) ethanol and then centrifuged for 3 seconds. The supernatant was removed; the particles were washed with 200 ul of 100% ethanol and centrifuged for 3 seconds. The supernatant was removed and 24 ul 100% ethanol was added and mixed by pipetting. The tube was placed in an ultrasonic cleaning bath for approximately 15 seconds to further resuspend the particles in the ethanol. While the tube was in the ultrasonic bath, 8 ul aliquots of suspended particles were removed and placed onto the center of macrocarrier disks that were held in a desiccator. Once the tungsten/DNA solution had dried onto the macrocarrier, it was placed in the bombardment chamber along with the plate of MM acetamide with spores and the bombardment process was performed using 1100 psi rupture discs according to the manufacturers instructions. After the bombardment of the plated spores with the tungsten/DNA particles, the plates were placed incubated at 28 C. Large transformed colonies were picked to fresh plates of MM acetamide after 5 days (Penttila et al., (1987) *Gene* 61:155-164).

The large colonies were compared to each other. The one dozen large colonies showing the most colony opacity were chosen for shake flask evaluation.

EXAMPLE 4

Fermentation of *Trichoderma reesei*

The dozen transformants chose for evaluation and the untransformed parent strain were transferred to individual PDA plates and grown to sporulation (7 to 10 days). Next they were grown in two stages in shake flasks. In the first stage the transformants and the parent were grown in 250 ml four baffled bottom shake flasks (Bellco Biotechnology) containing 50 ml of *T. reesei* Proflo Media. Inoculation was performed by transferring approximately 5 cm² of the sporulated mycelia and agar from the PDA plates. The flasks were grown for two days at 30° C. with a shaking speed of 250 rpm (1" diameter orbit) (Innova 4900 shaker incubator, New Brunswick Scientific).

*T. reesei* Proflo Media, per liter: alpha-lactose, 30 g; $(NH_4)_2 SO_4$, 6.5 g; $KH_2PO_4$, 2 g; $MgSO_4.7H_2O$, 0.3 g; $CaCL_2.2H_2O$, 0.26 g; 10% Tween 80, 2 ml; $FeSO_4.7H_2O$, 5 mg; $MnSO_4.H_2O$, 1.6 mg; $ZnSO_4.7H_2O$, 1.4 mg; Proflo, 22.5 g and $CaCO_3$, 0.72 g.

Next, 5 ml from the first stage shake flask was inoculated into a second stage shake flask consisting of a 250 ml four baffled bottom shake flask, containing 50 ml of Lactose defined Media. These flasks were grown for 5 days at 28° C. with a shaking speed of 175 rpm (5 cm diameter orbit) (Multitron shaker incubator, Infors AG, Bottmingen, Switzerland). Lactose defined media, per liter: $(NH_4)_2SO_4$, 5 g; PIPPS Buffers, 33 g; Bacto Casamino Acids, 9 g; $KH_2PO_4$, 4.5 g; $CaCL_2.2H_2O$, 1.32 g; $MgSO_4.7H_2O$, 1 g; Mazu DF204, 5 ml; 400× Salts Solution 2.5 ml; pH to 5.5; Sterile addition after autoclave and 40% lactose, 40 ml. 400× Salt Solution: citric acid (anhydrous), 175 g; $FeSO_4.7H_2O$, 200 g; $MnSO_4.H_2O$, 1.4 mg; $ZnSO_4.7H_2O$, 16 g; $CuSO_4.5H_2O$, 3.2 g and $H_3BO_3$, 0.8 g.

Figure 5:
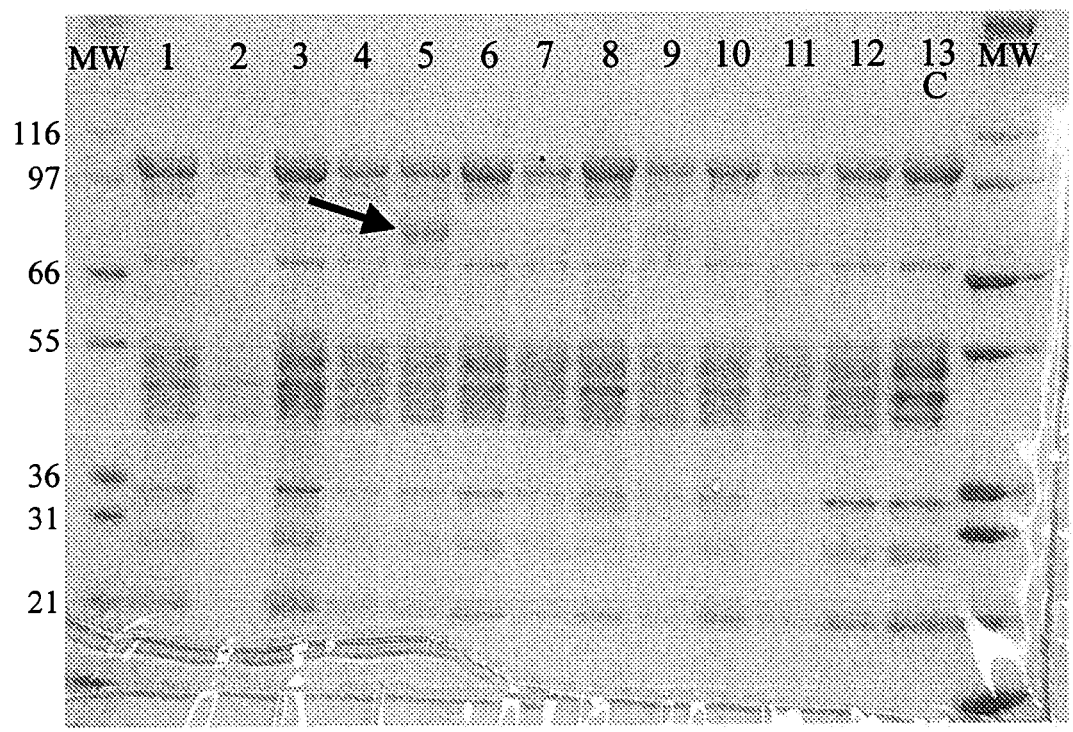
FIG. 5 illustrates NuPage gels of sample transformants, wherein transformants are represented in lanes 1-12 and the untransformed parent control is in lane 13. The Mark 12 molecular weight markers (Invitrogen) MW are observed on both ends of the gel. Standard bands are indicated in kDa on the left. The expressed *A. niger* alpha amylase is observed in lane 5 as indicated by the band marked with the arrow.

Five day samples were taken from the shake flasks. The supernate was separated from the mycelia by filtration through 0.45 um pore filters. Supernate samples were run on 4-12% NuPage Gels (Invitrogen), 1 mm thick using MOPS buffer and stained with SimplyBlue Safe Stain (Invitrogen) following the manufacturer's directions (FIG. 5). Transformants are observed in lanes 1-12 of the gel.

EXAMPLE 5

Raw Starch Hydrolyzing Activity of the *A. niger* Alpha-amylase

Figure 6:
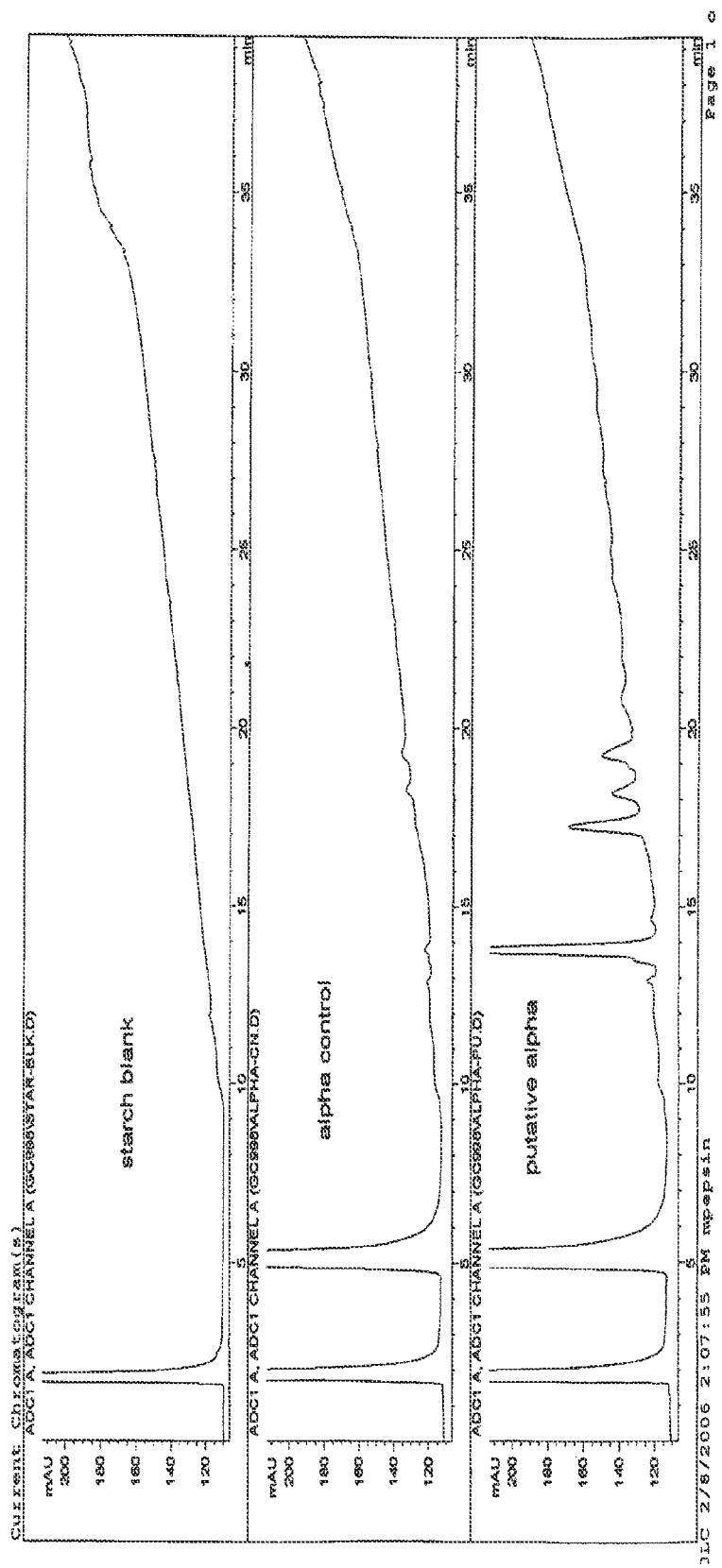
FIG. 6 illustrates raw starch degradation by the alpha-amylase represented in FIG. 3, (labeled putative alpha in the figure) compared to a starch blank and an alpha amylase control as measured by HPLC.

Samples, which were obtained as described in the examples above, were analyzed for raw starch degradation by HPAEC-PAD, using a Dionex PA1, with a sodium hydroxide/sodium acetate gradient. Two shake flask samples (control strain and strain containing the *A. niger* alpha-amylase of the invention (designated putative alpha-amylase)) wee first concentrated about 10 fold using a spin column. Fifty microliters of the concentrate were then added to 2 ml of 5% corn starch in a 100 mM sodium acetate, pH 4.5. the tubes were incubated overnight at 34° C., 250 rpm. Reaction tubes were spun the next morning, filtered and diluted. Ten microliters were injected into the HPLC and the results are illustrated in FIG. 6.

---

It is claimed:

1. An isolated DNA encoding an alpha-amylase having at least 98% sequence identity to SEQ ID NO: 3.

2. An expression vector comprising the DNA of claim 1.

3. An isolated host cell comprising the expression vector of claim 2.

4. The host cell of claim 3, wherein the host cell is a bacterial or fungal cell.

5. The host cell of claim 4, wherein the fungal cell is an *Aspergillus*, a *Trichoderma* or a *Fusarium* cell.

6. A cell culture comprising cells which express a heterologous alpha-amylase, said alpha-amylase comprising SEQ ID NO: 8.

7. The cell culture of claim 6, wherein the cells are *Trichoderma* or *Aspergillus* cells.

8. An isolated protein having alpha-amylase activity and comprising SEQ ID NO: 5.

9. The enzyme composition of claim 8 which is a starch hydrolyzing enzyme composition.

10. The enzyme composition of claim 8 which is a detergent composition.

11. The enzyme composition of claim 8 which is a cleaning composition.

12. The enzyme composition of claim 8 further comprising one or more additional enzymes selected from the group of glucoamylases, other amylases, proteases, lipases, pullulanases, xylanases, cellulases and combinations thereof.

* * * * *

SEQUENCE LISTING

```
<160> NUMBER OF SEQ ID NOS: 18

<210> SEQ ID NO 1
<211> LENGTH: 2365
<212> TYPE: DNA
<213> ORGANISM: Aspergillus niger

<400> SEQUENCE: 1
atgagactat cgacttcaag tctcttactt tccgtgtctc tgctggggaa gctggccctc      60
gggctgtcgg ctgcagaatg gcgcactcag tcgatttact tcctattgac ggatcggttc     120
ggtaggacgg acaattcgac gacagctaca tgcaatacgg gtgaccaagt acgttggtat     180
tgcaggactt ttatcattca tctactgact tgaatagatc tattgtggtg gtagttggca     240
agggatcatc aaccatgttt gtaaccgctc catactatct gctgtgcgcg tgtctgactt     300
tatttgctgc agctggatta tatccagggc atgggattca cggccatctg gatctcgcct     360
atcactgaac agctgcccca ggatactgct gatggtgaag cctaccatgg atattggcag     420
cagaagatgt atgcgttcct cctttccata tcgtaggctt actctcagac ggcgactgac     480
ttgacagata cgacgtgaac tccaacttcg gcactgcaga tgacctcaag tccctctcag     540
atgcgcttca tgcccgcgga atgtacctca tggtggacgt cgtccctaac cacatggtaa     600
gtgctgcttc agcatcctaa tcagtgaatt ccaagtgcca acgctaactg taccagggct     660
acgccggcaa cggcaacgat gtagactaca gcgtcttcga cccctttcgat tcctcctcct    720 acttccaccc atactgcctg atcacagatt gggacaactt gaccatggtc caagattgtt     780
gggagggtga caccatcgta tctctgccag acctaaacac caccgaaact gccgtgagaa     840
caatctggta tgactgggta gccgacctgg tatccaatta ttcaggtgcg aattgcaatc     900
```

```
caatctaaaa taatcatata ctaagtgaaa tcatcagtcg acggactccg catcgacagt    960
gtcctcgaag tcgaaccaga cttcttcccg ggctaccagg aagcagcggg tgtctactgc   1020
gtcggcgaag tcgacaacgg caaccctgcc ctcgactgcc cataccagga gtacctggac   1080
ggcgtcctca actatccgat gtacattccc ctacacatta ttcagatctt cgctaactcc   1140
aaaccagcta ctggcaactc ctctacgcct tcgaatcctc cagcggcagc atcagcgacc   1200
tctacaacat gatcaaatcc gtcgcaagcg actgctccga tccgacacta ctcggcaact   1260
tcatcgaaaa ccacgacaat ccccgttttg cctcgtatgt cccaccccct cccatccccct  1320
ccccacaatc acactcacta atgcatcaaa cagctacaca tccgactact cgcaagccaa   1380
aaacgtcctc agctacatct tcctctccga cggcatcccc atcgtctacg ccggcgaaga   1440
acagcactac tccggcggca aggtgcccta caaccgcgaa gcgacctggc tctcaggcta   1500
cgacacctcc gcagagctct acacctggat agccaccacg aacgcgatcc gcaaactagc   1560
catctcagct gactcggcct acattaccta cgcggttcgt ccttccctcc ccccacccct   1620
acaaacaccc ccacatacta caacatccc aataatgaaa tagaatgacg cattctacac    1680
cgacagcaac accatcgcaa tgcgcaaagg cacctcaggg agccaagtca tcaccgtcct   1740
ctccaacaaa ggctcctcag gaagcagcta caccctgacc ctcagcggaa gcggctatac   1800
atccggcacg aagctgatcg aagcgtatac atgcacgtcc gtgaccgtgg actcgagcgg   1860
cgatatcccc gtgccgatgg cgtcgggatt accgagagtt cttctccccg cgtccgtcgt   1920
cgatagctct tcgctctgtg gcgggagcgg aagtaattcc tcaactacaa ccacaacaac   1980
agctacctca tcttccactg cgacatccaa atccgcatca acctcgtcta cgtcgacggc   2040
atgcacagct acctctacct ccctcgcggt cacgttcgaa gagctcgtca cgactaccta   2100
cggggaggaa atctacctga gcggatcgat ctcccagctt ggggactggg atacgagtga   2160
tgcggtgaag atgtccgcgg atgattatac gtcgagtaat ccggagtggt cggttactgt   2220
gacgttgccg gtggggacaa cctttgagta taagtttatt aaggtggagt cggatgggac   2280
tgttacttgg gagagtgatc cgaatcggga gtatacggtg cccgagtgtg ggagtgggga   2340
gacggtggtt gacacttgga ggtaa                                         2365
```

<210> SEQ ID NO 2
<211> LENGTH: 1914
<212> TYPE: DNA
<213> ORGANISM: Aspergillus niger

<400> SEQUENCE: 2

```
atgagactat cgacttcaag tctcttactt tccgtgtctc tgctggggaa gctggccctc     60
gggctgtcgg ctgcagaatg gcgcactcag tcgatttact tcctattgac ggatcggttc    120
ggtaggacgg acaattcgac gacagctaca tgcaatacgg gtgaccaaat ctattgtggt    180
ggtagttggc aagggatcat caaccatctg gattatatcc agggcatggg attcacggcc    240
atctggatct cgcctatcac tgaacagctg ccccaggata ctgctgatgg tgaagcctac    300
catggatatt ggcagcagaa gatatacgac gtgaactcca acttcggcac tgcagatgac    360
ctcaagtccc tctcagatgc gcttcatgcc cgcggaatgt acctcatggt ggacgtcgtc    420
cctaaccaca tgggctacgc cggcaacggc aacgatgtag actacagcgt cttcgacccc    480
ttcgattcct cctcctactt ccacccatac tgcctgatca cagattggga caacttgacc    540
atggtccaag attgttggga gggtgacacc atcgtatctc tgccagacct aaacaccacc    600
gaaactgccg tgagaacaat ctggtatgac tgggtagccg acctggtatc caattattca    660
```

```
gtcgacggac tccgcatcga cagtgtcctc gaagtcgaac cagacttctt cccgggctac    720
caggaagcag cgggtgtcta ctgcgtcggc gaagtcgaca acggcaaccc tgccctcgac    780
tgcccatacc aggagtacct ggacggcgtc ctcaactatc cgatctactg caactcctc     840 tacgccttcg aatcctccag cggcagcatc agcgacctct acaacatgat caaatccgtc    900
gcaagcgact gctccgatcc gacactactc ggcaacttca tcgaaaacca cgacaatccc    960
cgttttgcct cctacacatc cgactactcg caagccaaaa acgtcctcag ctacatcttc    1020
ctctccgacg gcatccccat cgtctacgcc ggcgaagaac agcactactc cggcggcaag    1080
gtgccctaca accgcgaagc gacctggctc tcaggctacg acacctccgc agagctctac    1140
acctggatag ccaccacgaa cgcgatccgc aaactagcca tctcagctga ctcggcctac    1200
attacctacg cgaatgacgc attctacacc gacagcaaca ccatcgcaat gcgcaaaggc    1260
acctcaggga gccaagtcat caccgtcctc tccaacaaag gctcctcagg aagcagctac    1320
accctgaccc tcagcggaag cggctataca tccggcacga agctgatcga agcgtataca    1380
tgcacgtccg tgaccgtgga ctcgagcggc gatatccccg tgccgatggc gtcgggatta    1440
ccgagagttc ttctccccgc gtccgtcgtc gatagctctt cgctctgtgg cgggagcgga    1500
agtaattcct caactacaac cacaacaaca gctacctcat cttccactgc gacatccaaa    1560
tccgcatcaa cctcgtctac gtcgacggca tgcacagcta cctctacctc cctcgcggtc    1620
acgttcgaag agctcgtcac gactacctac ggggaggaaa tctacctgag cggatcgatc    1680
tcccagcttg gggactggga tacgagtgat gcggtgaaga tgtccgcgga tgattatacg    1740
tcgagtaatc cggagtggtc ggttactgtg acgttgccgg tggggacaac ctttgagtat    1800
aagtttatta aggtggagtc ggatgggact gttacttggg agagtgatcc gaatcgggag    1860
tatacggtgc cgagtgtggg gagtgggag acggtggttg acacttggag gtaa          1914
```

<210> SEQ ID NO 3
<211> LENGTH: 637
<212> TYPE: PRT
<213> ORGANISM: Aspergillus niger

<400> SEQUENCE: 3

```
Met Arg Leu Ser Thr Ser Ser Leu Leu Leu Ser Val Ser Leu Leu Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asn Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ala Asp
                85                  90                  95

Gly Glu Ala Tyr His Gly Tyr Trp Gln Gln Lys Ile Tyr Asp Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
```

-continued

```
            145                 150                 155                 160
        Phe Asp Ser Ser Tyr Phe His Pro Tyr Cys Leu Ile Thr Asp Trp
                        165                 170                 175

Asp Asn Leu Thr Met Val Gln Asp Cys Trp Glu Gly Asp Thr Ile Val
                        180                 185                 190

Ser Leu Pro Asp Leu Asn Thr Thr Glu Thr Ala Val Arg Thr Ile Trp
                        195                 200                 205

Tyr Asp Trp Val Ala Asp Leu Val Ser Asn Tyr Ser Val Asp Gly Leu
                        210                 215                 220

Arg Ile Asp Ser Val Leu Glu Val Glu Pro Asp Phe Phe Pro Gly Tyr
        225                 230                 235                 240

Gln Glu Ala Ala Gly Val Tyr Cys Val Gly Glu Val Asp Asn Gly Asn
                        245                 250                 255

Pro Ala Leu Asp Cys Pro Tyr Gln Glu Tyr Leu Asp Gly Val Leu Asn
                        260                 265                 270

Tyr Pro Ile Tyr Trp Gln Leu Leu Tyr Ala Phe Glu Ser Ser Ser Gly
                        275                 280                 285

Ser Ile Ser Asp Leu Tyr Asn Met Ile Lys Ser Val Ala Ser Asp Cys
                        290                 295                 300

Ser Asp Pro Thr Leu Leu Gly Asn Phe Ile Glu Asn His Asp Asn Pro
        305                 310                 315                 320

Arg Phe Ala Ser Tyr Thr Ser Asp Tyr Ser Gln Ala Lys Asn Val Leu
                        325                 330                 335

Ser Tyr Ile Phe Leu Ser Asp Gly Ile Pro Ile Val Tyr Ala Gly Glu
                        340                 345                 350

Glu Gln His Tyr Ser Gly Gly Lys Val Pro Tyr Asn Arg Glu Ala Thr
                        355                 360                 365

Trp Leu Ser Gly Tyr Asp Thr Ser Ala Glu Leu Tyr Thr Trp Ile Ala
                        370                 375                 380

Thr Thr Asn Ala Ile Arg Lys Leu Ala Ile Ser Ala Asp Ser Ala Tyr
        385                 390                 395                 400

Ile Thr Tyr Ala Asn Asp Ala Phe Tyr Thr Asp Ser Asn Thr Ile Ala
                        405                 410                 415

Met Arg Lys Gly Thr Ser Gly Ser Gln Val Ile Thr Val Leu Ser Asn
                        420                 425                 430

Lys Gly Ser Ser Gly Ser Ser Tyr Thr Leu Thr Leu Ser Gly Ser Gly
                        435                 440                 445

Tyr Thr Ser Gly Thr Lys Leu Ile Glu Ala Tyr Thr Cys Thr Ser Val
                        450                 455                 460

Thr Val Asp Ser Ser Gly Asp Ile Pro Val Pro Met Ala Ser Gly Leu
        465                 470                 475                 480

Pro Arg Val Leu Leu Pro Ala Ser Val Val Asp Ser Ser Leu Cys
                        485                 490                 495

Gly Gly Ser Gly Ser Asn Ser Ser Thr Thr Thr Thr Thr Ala Thr
                        500                 505                 510

Ser Ser Ser Thr Ala Thr Ser Lys Ser Ala Ser Thr Ser Ser Thr Ser
                        515                 520                 525

Thr Ala Cys Thr Ala Thr Ser Thr Ser Leu Ala Val Thr Phe Glu Glu
                        530                 535                 540

Leu Val Thr Thr Thr Tyr Gly Glu Glu Ile Tyr Leu Ser Gly Ser Ile
        545                 550                 555                 560

Ser Gln Leu Gly Asp Trp Asp Thr Ser Asp Ala Val Lys Met Ser Ala
                        565                 570                 575
```

```
Asp Asp Tyr Thr Ser Ser Asn Pro Glu Trp Ser Val Thr Val Thr Leu
            580                 585                 590

Pro Val Gly Thr Thr Phe Glu Tyr Lys Phe Ile Lys Val Glu Ser Asp
            595                 600                 605

Gly Thr Val Thr Trp Glu Ser Asp Pro Asn Arg Glu Tyr Thr Val Pro
            610                 615                 620

Glu Cys Gly Ser Gly Thr Val Val Asp Thr Trp Arg
625                 630                 635

<210> SEQ ID NO 4
<211> LENGTH: 21
<212> TYPE: PRT
<213> ORGANISM: Aspergillus niger

<400> SEQUENCE: 4

Met Arg Leu Ser Thr Ser Ser Leu Leu Leu Ser Val Ser Leu Leu Gly
1               5                   10                  15

Lys Leu Ala Leu Gly
            20

<210> SEQ ID NO 5
<211> LENGTH: 478
<212> TYPE: PRT
<213> ORGANISM: Aspergillus niger

<400> SEQUENCE: 5

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
            35                  40                  45

Leu Asp Tyr Ile Gln Gly Met Gly Phe Thr Ala Ile Trp Ile Ser Pro
50                  55                  60

Ile Thr Glu Gln Leu Pro Gln Asp Thr Ala Asp Gly Glu Ala Tyr His
65              70                  75                  80

Gly Tyr Trp Gln Gln Lys Ile Tyr Asp Val Asn Ser Asn Phe Gly Thr
            85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
            115                 120                 125

Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
            165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
            195                 200                 205

Leu Glu Val Glu Pro Asp Phe Phe Pro Gly Tyr Gln Glu Ala Ala Gly
            210                 215                 220

Val Tyr Cys Val Gly Glu Val Asp Asn Gly Asn Pro Ala Leu Asp Cys
225                 230                 235                 240
```

```
Pro Tyr Gln Glu Tyr Leu Asp Gly Val Leu Asn Tyr Pro Ile Tyr Trp
            245                 250                 255

Gln Leu Leu Tyr Ala Phe Glu Ser Ser Gly Ser Ile Ser Asp Leu
        260                 265                 270

Tyr Asn Met Ile Lys Ser Val Ala Ser Asp Cys Ser Asp Pro Thr Leu
            275                 280                 285

Leu Gly Asn Phe Ile Glu Asn His Asp Asn Pro Arg Phe Ala Ser Tyr
        290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
                325                 330                 335

Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Ala Tyr Ile Thr Tyr Ala Asn
        370                 375                 380

Asp Ala Phe Tyr Thr Asp Ser Asn Thr Ile Ala Met Arg Lys Gly Thr
385                 390                 395                 400

Ser Gly Ser Gln Val Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Ser
        435                 440                 445

Gly Asp Ile Pro Val Pro Met Ala Ser Gly Leu Pro Arg Val Leu Leu
    450                 455                 460

Pro Ala Ser Val Val Asp Ser Ser Ser Leu Cys Gly Gly Ser
465                 470                 475

<210> SEQ ID NO 6
<211> LENGTH: 31
<212> TYPE: PRT
<213> ORGANISM: Aspergillus niger

<400> SEQUENCE: 6

Gly Ser Asn Ser Ser Thr Thr Thr Thr Thr Ala Thr Ser Ser Ser
1               5                   10                  15

Thr Ala Thr Ser Lys Ser Ala Ser Thr Ser Ser Thr Ser Thr Ala
            20                  25                  30

<210> SEQ ID NO 7
<211> LENGTH: 107
<212> TYPE: PRT
<213> ORGANISM: Aspergillus niger

<400> SEQUENCE: 7

Cys Thr Ala Thr Ser Thr Ser Leu Ala Val Thr Phe Glu Glu Leu Val
1               5                   10                  15

Thr Thr Thr Tyr Gly Glu Glu Ile Tyr Leu Ser Gly Ser Ile Ser Gln
            20                  25                  30

Leu Gly Asp Trp Asp Thr Ser Asp Ala Val Lys Met Ser Ala Asp Asp
        35                  40                  45

Tyr Thr Ser Ser Asn Pro Glu Trp Ser Val Thr Val Thr Leu Pro Val
    50                  55                  60
```

```
Gly Thr Thr Phe Glu Tyr Lys Phe Ile Lys Val Glu Ser Asp Gly Thr
65                  70                  75                  80

Val Thr Trp Glu Ser Asp Pro Asn Arg Glu Tyr Thr Val Pro Glu Cys
                85                  90                  95

Gly Ser Gly Glu Thr Val Val Asp Thr Trp Arg
            100                 105

<210> SEQ ID NO 8
<211> LENGTH: 616
<212> TYPE: PRT
<213> ORGANISM: Aspergillus niger

<400> SEQUENCE: 8

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
                20                  25                  30

Gly Asp Gln Ile Tyr Cys Gly Gly Ser Trp Gln Gly Ile Ile Asn His
            35                  40                  45

Leu Asp Tyr Ile Gln Gly Met Gly Phe Thr Ala Ile Trp Ile Ser Pro
50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
            115                 120                 125

Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
            195                 200                 205

Leu Glu Val Glu Pro Asp Phe Phe Pro Gly Tyr Gln Glu Ala Ala Gly
        210                 215                 220

Val Tyr Cys Val Gly Glu Val Asp Asn Gly Asn Pro Ala Leu Asp Cys
225                 230                 235                 240

Pro Tyr Gln Glu Tyr Leu Asp Gly Val Leu Asn Tyr Pro Ile Tyr Trp
                245                 250                 255

Gln Leu Leu Tyr Ala Phe Glu Ser Ser Gly Ser Ile Ser Asp Leu
            260                 265                 270

Tyr Asn Met Ile Lys Ser Val Ala Ser Asp Cys Ser Asp Pro Thr Leu
            275                 280                 285

Leu Gly Asn Phe Ile Glu Asn His Asp Asn Pro Arg Phe Ala Ser Tyr
        290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
```

```
            325                 330                 335
Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
            355                 360                 365

Arg Lys Leu Ala Ile Ser Ala Asp Ser Ala Tyr Ile Thr Tyr Ala Asn
370                 375                 380

Asp Ala Phe Tyr Thr Asp Ser Asn Thr Ile Ala Met Arg Lys Gly Thr
385                 390                 395                 400

Ser Gly Ser Gln Val Ile Thr Val Leu Ser Asn Lys Gly Ser Ser Gly
            405                 410                 415

Ser Ser Tyr Thr Leu Thr Leu Ser Gly Ser Tyr Thr Ser Gly Thr
            420                 425                 430

Lys Leu Ile Glu Ala Tyr Thr Cys Thr Ser Val Thr Val Asp Ser Ser
            435                 440                 445

Gly Asp Ile Pro Val Pro Met Ala Ser Gly Leu Pro Arg Val Leu Leu
450                 455                 460

Pro Ala Ser Val Val Asp Ser Ser Ser Leu Cys Gly Gly Ser Gly Ser
465                 470                 475                 480

Asn Ser Ser Thr Thr Thr Thr Thr Ala Thr Ser Ser Ser Thr Ala
            485                 490                 495

Thr Ser Lys Ser Ala Ser Thr Ser Ser Thr Thr Ala Cys Thr Ala
            500                 505                 510

Thr Ser Thr Ser Leu Ala Val Thr Phe Glu Glu Leu Val Thr Thr Thr
            515                 520                 525

Tyr Gly Glu Glu Ile Tyr Leu Ser Gly Ser Ile Ser Gln Leu Gly Asp
            530                 535                 540

Trp Asp Thr Ser Asp Ala Val Lys Met Ser Ala Asp Asp Tyr Thr Ser
545                 550                 555                 560

Ser Asn Pro Glu Trp Ser Val Thr Val Thr Leu Pro Val Gly Thr Thr
            565                 570                 575

Phe Glu Tyr Lys Phe Ile Lys Val Glu Ser Asp Gly Thr Val Thr Trp
            580                 585                 590

Glu Ser Asp Pro Asn Arg Glu Tyr Thr Val Pro Glu Cys Gly Ser Gly
            595                 600                 605

Glu Thr Val Val Asp Thr Trp Arg
            610                 615

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
caccatgaga ctatcgactt caag                                    24

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
ttacctccaa gtgtcaacca ccgtctc                                 27
```

```
<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
tagagttgtg aagtcggtaa tcccgc                                        26

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
cgatagtctc attgactatt gggtttctgt gcctc                              35

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
acccaatagt caatgagact atcgacttca ag                                 32

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
tcgcacggag ctttacctcc aagtgtcaac caccgtctc                          39

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
ttggaggtaa agctccgtgc gaaagcctga c                                  31

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
tactgggata cacgaagagc gg                                            22

<210> SEQ ID NO 17
<211> LENGTH: 26
<212> TYPE: DNA
<213> ORGANISM: Artificial Sequence
<220> FEATURE:
```

```
<223> OTHER INFORMATION: primer

<400> SEQUENCE: 17
gtgaagtcgg taatcccgct gtatag                                    26

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
ggatacacga agagcggcga ttc                                       23
```